United States Patent
Webber et al.

(10) Patent No.: US 9,943,386 B2
(45) Date of Patent: Apr. 17, 2018

(54) MOLD WITH WEAKENED AREAS

(71) Applicant: Align Technology, Inc., San Jose, CA (US)

(72) Inventors: Peter Webber, Lafayette, CA (US); Rohit Tanugula, San Jose, CA (US); Shiva P. Sambu, Milpitas, CA (US); Crystal Tjhia, Sunnyvale, CA (US)

(73) Assignee: Align Technology, Inc., San Jose, CA (US)

( * ) Notice: Subject to any disclaimer, the term of this patent is extended or adjusted under 35 U.S.C. 154(b) by 321 days.

(21) Appl. No.: 14/716,601

(22) Filed: May 19, 2015

(65) Prior Publication Data

US 2015/0335404 A1    Nov. 26, 2015

Related U.S. Application Data

(60) Provisional application No. 62/001,489, filed on May 21, 2014.

(51) Int. Cl.
| | | |
|---|---|---|
| *A61C 7/08* | (2006.01) | |
| *A61C 9/00* | (2006.01) | |
| *B33Y 30/00* | (2015.01) | |
| *B33Y 10/00* | (2015.01) | |

(52) U.S. Cl.
CPC .................. *A61C 9/00* (2013.01); *A61C 7/08* (2013.01); *B33Y 10/00* (2014.12); *B33Y 30/00* (2014.12)

(58) Field of Classification Search
None
See application file for complete search history.

(56) References Cited

U.S. PATENT DOCUMENTS

| | | | |
|---|---|---|---|
| 2001/0002014 A1 | 5/2001 | Champagnon et al. | |
| 2004/0191728 A1 | 9/2004 | Miller | |
| 2008/0233528 A1* | 9/2008 | Kim ....................... | A61C 7/146 433/2 |
| 2011/0304075 A1 | 12/2011 | Catoen et al. | |

FOREIGN PATENT DOCUMENTS

WO          00/32132 A1       6/2000

OTHER PUBLICATIONS

"Malocclusion." Merriam-Webster.com. Merriam-Webster, n.d. Web. Aug. 17, 2017 accessed at merriam-webster.com on Aug. 17, 2017.*
International Preliminary Report on Patentability for PCT Application No. PCT/IB2015/000744 dated Aug. 18, 2016.
International Search Report and Written Opinion for PCT/IB2015/000744 dated Dec. 8, 2015.
Bjorn, Ludwig et al. "Selbstligierende Brackets: Konzepte and behandlung" machine translated as "Self-ligating Brackets: Concepts and Treatment", Dec. 16, 2009, pp. 94-96, Thieme Verlag, XP055205560, ISBN: 978-3-13-149701-7; includes a German transcription and machine translation of the referenced pages.

* cited by examiner

*Primary Examiner* — Alison L Hindenlang
*Assistant Examiner* — Jamel M Nelson
(74) *Attorney, Agent, or Firm* — Lowenstein Sandler LLP

(57) ABSTRACT

A breakable or deflectable mold includes a first section, a second section, and a weakened region that joins the first section to the second section. The weakened region is breakable or deflectable to enable the first section to be removed independently of the second section after a shell is formed over the breakable mold.

10 Claims, 13 Drawing Sheets

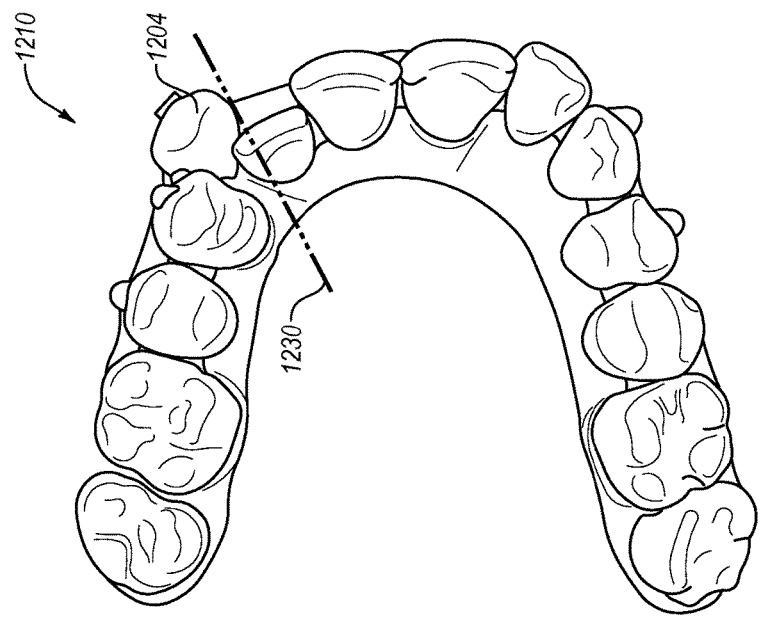
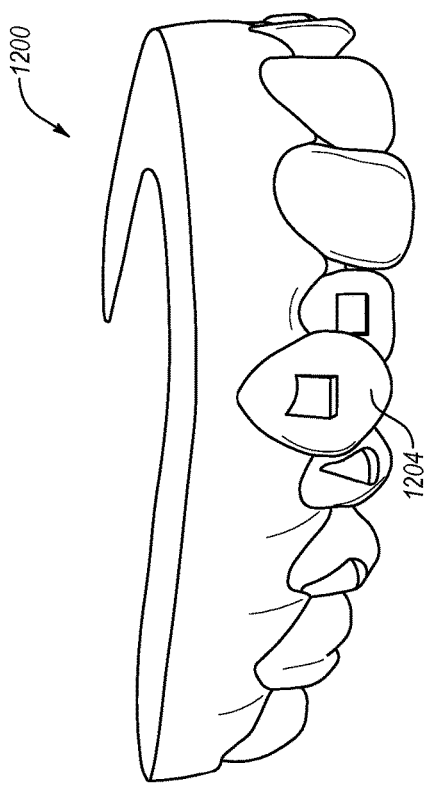
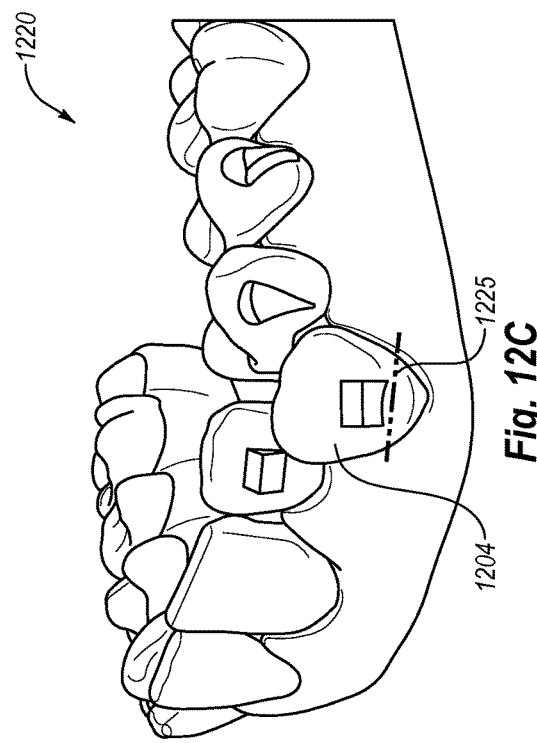

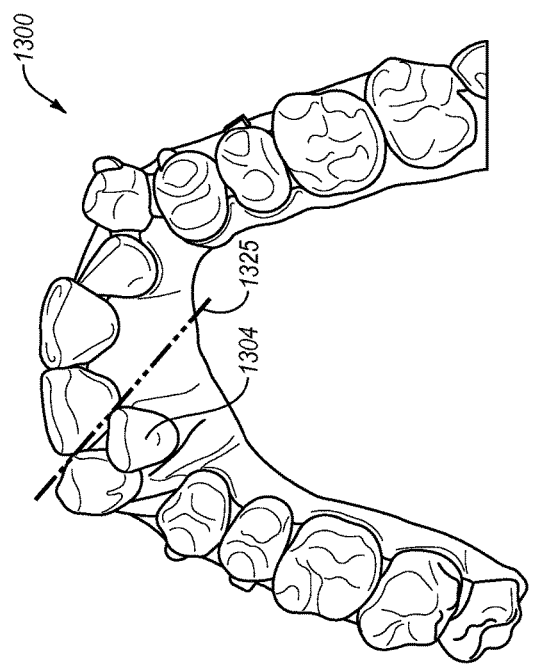
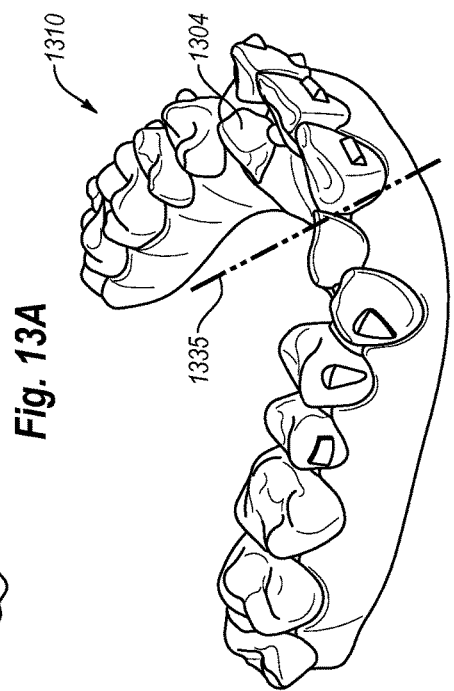
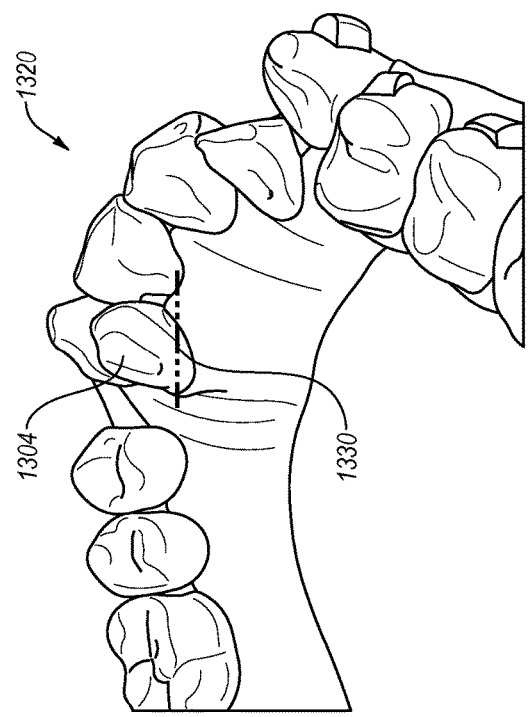
Fig. 13A
Fig. 13B
Fig. 13C

MOLD WITH WEAKENED AREAS

RELATED APPLICATIONS

This patent application claims the benefit under 35 U.S.C. § 119(e) of U.S. Provisional Application No. 62/001,489, filed May 21, 2014.

TECHNICAL FIELD

Embodiments of the present invention relate to the field of rapid prototyping molds and, in particular, to a breakable mold formed using a rapid prototyping technique.

BACKGROUND

For some applications, shells are formed around molds to achieve a negative of the mold. The shells are then removed from the molds to be further used for various applications. One example application in which a shell is formed around a mold and then later used is corrective dentistry or orthodontic treatment. In such an application, the mold is of a dental arch for a patient and the shell is an aligner to be used for aligning one or more teeth of the patient.

One challenge with molds used to form shells is the subsequent removal of the sheds from the molds. In order to ensure that a shell will be removable from a mold without damaging or permanently deforming the shell, the shapes and types of features that are included in the mold may be limited. For example, features with significant undercuts (also referred to as negative inclination) and/or complex features may impair the removal of the shell from the mold.

BRIEF DESCRIPTION OF THE DRAWINGS

The present invention is illustrated by way of example, and not by way of limitation, in the figures of the accompanying drawings.

FIG. 12A illustrates a first view of an example breakable mold of a dental arch with an ectopic tooth.

FIG. 12B illustrates a second view of the example breakable mold of FIG. 12A.

FIG. 12C illustrates a third view of the example breakable mold of FIG. 12A.

FIG. 13A illustrates a first view of an example breakable mold of a dental arch with an out of arch tooth.

FIG. 13B illustrates a second view of the example breakable mold of FIG. 13A.

FIG. 13C illustrates a third view of the example breakable mold of FIG. 13A.

DETAILED DESCRIPTION

Figure 1:
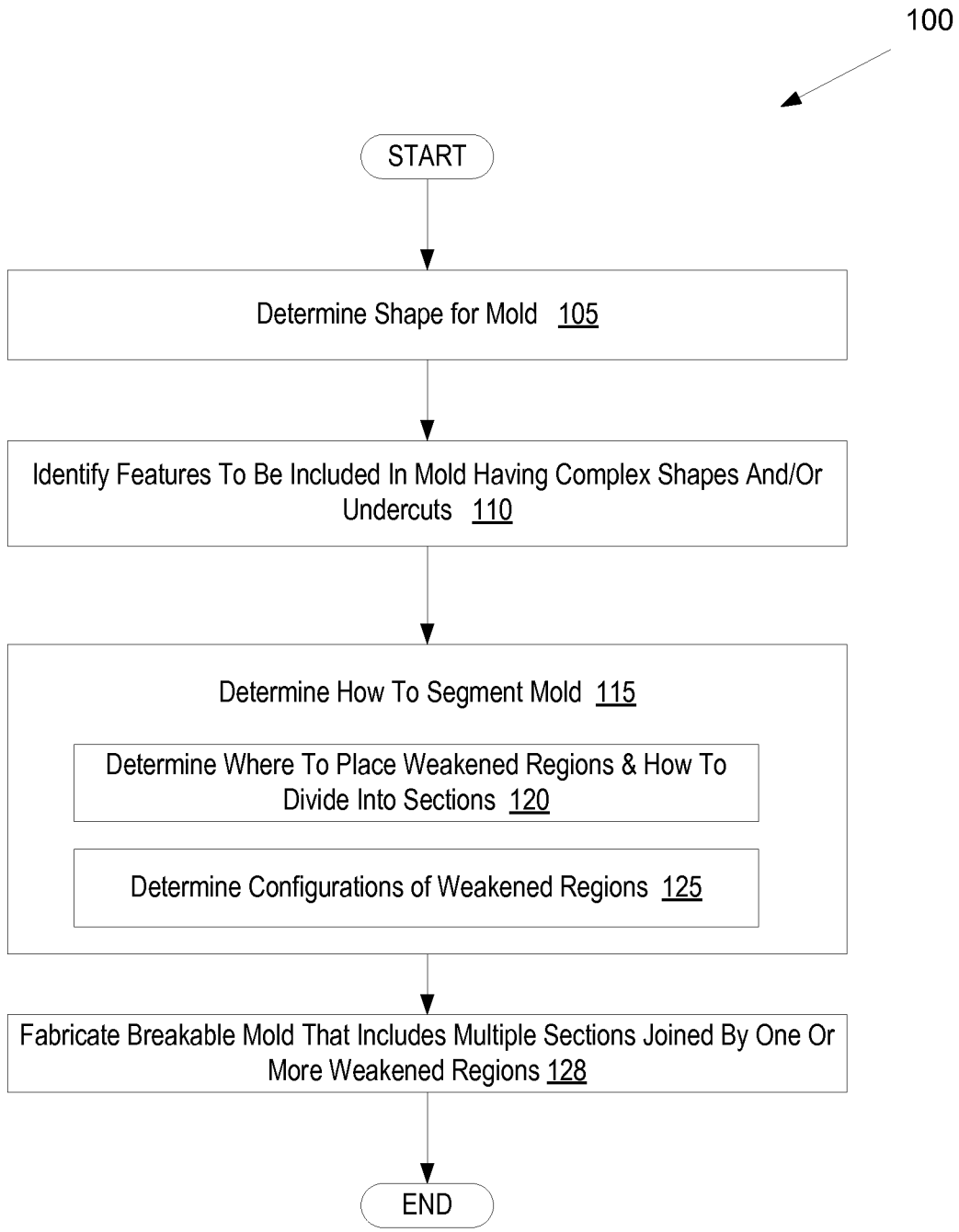
FIG. 1 illustrates a flow diagram for a method of fabricating a breakable mold, in accordance with one embodiment.

Described herein are embodiments of breakable and deflectable molds and methods of manufacturing and using such breakable and deflectable molds. Breakable and deflectable molds having a segmented configuration may be designed, fabricated and used. The segmented configuration may include multiple sections joined by weakened regions. The weakened regions may be placed relative to (e.g., around) features with undercuts or negative inclinations. For example, a breakable or deflectable mold may be sectioned into two or more weakly joined sections, where one section is on a first side of a feature with an undercut (e.g., adjacent to the feature) and the second section is on a second side of the feature with the undercut (e.g., under the feature). The breakable or deflectable mold may be broken or deflected at the weakened regions during the forming of a shell on the breakable mold or after the shell has been formed on the breakable mold (e.g., during removal of the shell from the breakable or deflectable mold). The weakened regions may break or deflect by application of a force that is less than a force that would cause the shell to be damaged or permanently deformed. That way, the weakened regions will break or deflect before the shell deforms or breaks. The breaking or deflecting of the weakened regions causes the mold to be at least partially separated into the constituent sections (e.g., fully separated for a breakable mold or partially separated for a deflectable mold). In some instances, one or more sections may not completely separate from the shell and/or other sections of the mold. For example, a section may mostly separate from another section, but leave a point of connection. This may permit additional deflection and/or freedom for the shell to be removed without damage. Each of the sections may then be removed from the shell independently of the other sections.

Use of a breakable or deflectable mold in accordance with embodiments herein enables complex features (e.g., features with a rough surface texture) and/or features with significant undercuts to be incorporated into formed shells. For example, if the breakable or deflectable mold is of a dental arch for a patient and the shell is an orthodontic aligner to be used for aligning one or more teeth of the patient, then the breakable or deflectable mold enables the aligner to correct dental problems such as very crowded teeth, proclined teeth, retroclined teeth, ectopic teeth, out of arch teeth, and so on. Use of a breakable or deflectable mold also makes removal of the shell from the mold easier in other instances. The shell may also be an orthodontic retainer or an orthodontic splint to be used for at least one of retaining, or positioning one or more teeth of the patient. The term aligner is used herein to refer to an orthodontic aligner, retainer and/or splint that can perform one or more of aligning teeth, retaining teeth and positioning teeth. Without the breakable or deflectable mold, the ability to create aligners with complex features that can facilitate correction of such dental problems can be impaired. Additionally, use of breakable or deflectable molds as described herein enables enhanced features with moderate to significant undercuts to be placed on a patient's teeth (and included in the mold). Such enhanced features may facilitate dental correction by enabling the treatment of different and/or complex dental problems. Moreover, use of the breakable or deflectable molds may minimize or eliminate damage caused to shells during removal of the molds from the shells, thereby reducing an amount of scrapped product and therefore overall cost.

Breakable and deflectable molds of dental arches for the production of orthodontic aligners are described with reference to various embodiments herein. However, it should be understood that breakable and deflectable molds may also be produced for other purposes (e.g., for molding any other desired plastic item).

Embodiments are discussed herein with reference to breakable molds, and to forming shells over such breakable molds. Such breakable molds include at least two sections that are separated by a weakened region that can break prior to removal of a shell from the breakable molds. However, it should be understood that embodiments also extend to deflectable molds. Deflectable molds are substantially similar to the breakable molds discussed herein, except that the discussed weakened regions may not break. For such embodiments, the weakened regions may bend or deflect during removal of the shell from the mold. This deflection of the weakened regions may enable the deflectable mold to be removed from the shell in spite of features in the deflectable mold that include negative inclination or an undercut. For example, a practitioner may apply a force to a first section of the deflectable mold that deflects a weakened region connecting the first section to a second section, thereby causing the first section to partially separate from the second section. This force may cause the first section to be substantially removed or separated from the shell before the second section begins to separate from the shell. Accordingly, it should be understood that all discussions of breakable molds provided herein also apply to deflectable molds.

FIG. 1 illustrates a flow diagram for a method 100 of fabricating a breakable mold, in accordance with one embodiment. In some embodiments, one or more operations of method 100 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 100 may be performed by a mold modeling module such as mold modeling module 1450 of FIG. 14. Additionally, some operations may be performed by a fabrication machine based on instructions received from processing logic. Some operations may alternately be performed by a user (e.g., based on user interaction with a mold modeling module or drafting program).

At block 105 of method 100, a shape of a mold is determined. In one embodiment, the shape is determined based on a scan of an object to be modeled. In the example of orthodontics, an intraoral scan of a patient's dental arch may be performed to generate a three dimensional (3D) virtual model of the patient's dental arch. For example, a full scan of the mandibular and/or maxillary arches of a patient may be performed to generate 3D virtual models thereof. The intraoral scan may be performed by creating multiple overlapping intraoral images from different scanning stations and then stitching together the intraoral images to provide a composite 3D virtual model. In other applications, virtual 3D models may also be generated based on scans of an object to be modeled or based on use of computer aided drafting techniques (e.g., to design the virtual 3D mold). Alternatively, an initial negative mold may be generated from an actual object to be modeled. The negative mold may then be scanned to determine a shape of a positive mold that will be produced.

Referring back to the example of orthodontics, multiple different molds may be generated for a single patient. A first mold is a model of a patient's dental arch and/or teeth as they presently exist, and a final mold is a model of the patient's dental arch and/or teeth after correction of one or more teeth and/or a jaw. Multiple intermediate molds may be modeled, each of which may be incrementally different from previous molds. Aligners may be formed from each mold to provide forces to move the patients teeth. The shape of the final mold and each intermediate mold may be determined by computing the progression of tooth movement throughout orthodontic treatment from initial tooth placement and orientation to final corrected tooth placement and orientation. Each mold may be used to fabricate an aligner that will apply forces to the patients teeth at a particular stage of the orthodontic treatment.

A shell can be designed to contain features (bumps, protrusions, wings, etc.) that are non-natural to the patient's dentition. These features may facilitate the application of particular desired forces to reposition teeth or position the jaw. These features may be included in the shape of the mold in order to manufacture the aligner shell.

In some instances, a dental practitioner may form attachments or features on some of a patient's teeth. These additional non-naturally occurring features may be used to facilitate the application of particular desired forces on the patient's teeth to reposition the teeth (e.g., to rotate and or move the teeth). The features may also apply forces to facilitate jaw movement. These attachments or features may include small, medium and large bumps, protrusions, wings, etc. that are formed from a hard composite material that adheres to the patient's teeth. Such features may be included in the determined shape of the mold. For example, these features may be placed before the dental arch of the patient is scanned, and thus may be reflected in a 3D virtual model of the dental arch.

Additionally, or alternatively, features can be added in a model (e.g., a 3D model generated based on a 3D intraoral scan of a patient's jaw or other dental site). The breakable or deflectable mold generated from the model would then include the features even if those features are not present in the patient's mouth. Accordingly, features can be added before or after intraoral scanning is performed.

At block 110, one or more features of the determined shape for the mold that have complex shapes and/or undercuts are identified. In one embodiment, processing logic identifies such features. For example, processing logic may process a 3D virtual model to identify all features having undercuts that meet some threshold. The threshold may be a particular amount of undercut (e.g., 0.2 mm of undercut, 0.4 mm of undercut, 1.0 mm of undercut, etc.). Additionally, multiple different thresholds may be used to identify features that might be problematic. Alternatively or additionally, a dental practitioner may identify complex features and/or features with undercuts. For example, the dental practitioner may highlight or delineate such features on a 3D virtual model using a drawing tool and/or a computer aided drafting application (e.g., using a model modeling module). Some examples of notable features that might have undercuts that are pronounced enough to cause problems include attachments placed by the dental practitioner, crowded teeth, proclined teeth, retroclined teeth, ectopic teeth, out of arch teeth, and so on.

At block 115, a determination is made of how to segment the virtual 3D mold to form a breakable mold (or deflectable mold). In one embodiment, such a determination is made by processing logic. For example, at block 120 processing logic or a dental practitioner may determine where to place weakened regions relative to the identified potentially problematic features, and may divide the virtual 3D mold into multiple sections that are joined by the weakened regions. In one embodiment, processing logic places one or more weakened regions around a problematic feature (e.g., a feature with an undercut and/or a complex shape) so that the problematic feature is included in a separate section than the rest of the mold. In a simple example, a mold may be divided into two sections, where a first section is on a first side of the feature and a second section is opposite the first section relative to the feature (e.g., on an opposite side of the feature).

Weakened regions may be achieved based on at least one of a weakening geometry, weakening build parameters, or materials that introduce weakening. For example, the strength of a weakened region may be controlled by modifying the length, width, height and/or number of support structures (e.g., support struts) that are included in a weakened region. The locations, dimensions, and strengths of the weakened regions maybe important to the function of the breakable mold. In one embodiment, the weakened regions should be designed to withstand the forces and stresses of thermoforming or pressure forming, while also being weak enough to later break apart when manually manipulated by a technician or computer controlled robotic manipulator. Additionally, the weakened regions should be configured such that they will not materially affect a final shape of the shell (e.g., cause imperfections or undesirable artifacts in a region of the shell formed over the weakened region). For example, the portion of the weakened region that will interface with the shell may be solid (e.g., in the example of weakened region that includes a cut or gap that does not extend to one surface of the breakable mold), in other words, the weakened region may include a void or a cut at a cross section between two sections in the breakable mold that extends through less than an entirety of the breakable mold at the cross section. In another example, a gap or void between two sections may extend to the surface of the breakable mold that interfaces with the shell, but the gap may be narrow enough so as not to cause artifacts in the shell formed on the breakable mold.

At block 125, the processing logic or a technician may determine configurations for the weakened regions that are to join the sections of the mold. This may include determining the shapes of the weakened regions and strengths of the weakened regions (e.g., that control how much force is necessary to break the weakened region) as wet as how each of the weakened regions is to be weakened. For example, one type of weakened region is a cut that extends most of the way through the mold. The cut may extend close to, but not penetrate, an upper surface of the mold that with contact a shell. Another type of weakened region is a void separating two sections with one or multiple support structures that bridge the void. Another type of weakened region is a series of perforations between two or more sections. Other types of weakened regions are also possible.

At block 128, the breakable mold is fabricated. In one embodiment, the breakable mold is fabricated based on a 3D virtual model of the breakable mold. In one embodiment, the 3D virtual model includes each of the sections of the breakable mold as well as the weakened regions. Accordingly, the breakable mold may be manufactured as a signal uniform body with these sections and weakened regions built into the design of the breakable mold. Alternatively, or additionally, one or more weakened regions may be introduced to the breakable mold and/or the breakable mold may be divided into one or more sections via a post processing procedure. For example, one or more cuts, perforations, holes, etc. may be formed in the breakable mold using a saw, a drill, a laser cutter, a plasma cutter, a knife, etc. after the breakable mold has been formed.

In one embodiment, the breakable mold is fabricated using a rapid prototyping manufacturing technique. One example of a rapid prototyping manufacturing technique is 3D printing. 3D Printing includes any layer-based additive manufacturing processes. A 3D printer may receive an input of the 3D virtual model of the breakable mold (e.g., as a computer aided drafting (CAD) file or 3D printable file such as a stereolithography (STL) file), and may use the 3D virtual model to create the breakable mold. 3D printing may be achieved using an additive process, where successive layers of material are formed in proscribed shapes. 3D printing may be performed using extrusion deposition, granular materials binding, lamination, photopolymerization, or other techniques.

In one embodiment, stereolithography (SLA), also known as optical fabrication solid imaging, is used to fabricate an SLA breakable mold. In SLA, the breakable mold is fabricated by successively printing thin layers of a photo-curable material (e.g., a polymeric resin) on top of one another. A platform rests in a bath of a liquid photopolymer or resin just below a surface of the bath. A light source (e.g., an ultraviolet laser) traces a pattern over the platform, curing the photopolymer where the light source is directed, to form a first layer of the breakable mold. The platform is lowered incrementally, and the light source traces a new pattern over the platform to form another layer of the breakable mold at each increment. This process repeats until the breakable mold is completely fabricated. Each layer may have a thickness of between 25 microns and 200 microns. Once all of the layers of the breakable mold are formed, the breakable mold may be cleaned and cured.

In one embodiment, the breakable or deflectable mold is generated as multiple separate molds that are then joined together. In such an embodiment, two or more sections may be manufactured as separate molds. These separate molds may then be joined together in a manner that enables them to later deflect from one another or break apart. Thus, the intersections between the separate molds/sections may form the weakened regions. In one example, different sections are joined by an elastic or flexible glue to enable deflection. In another example, different sections are joined by a relatively weak glue that will stop securing the sections together when sufficient force is applied (e.g., during removal of a shell from the mold). In another example, the different sections interlock in a manner such that they are separable when appropriate force is applied.

Figure 2:
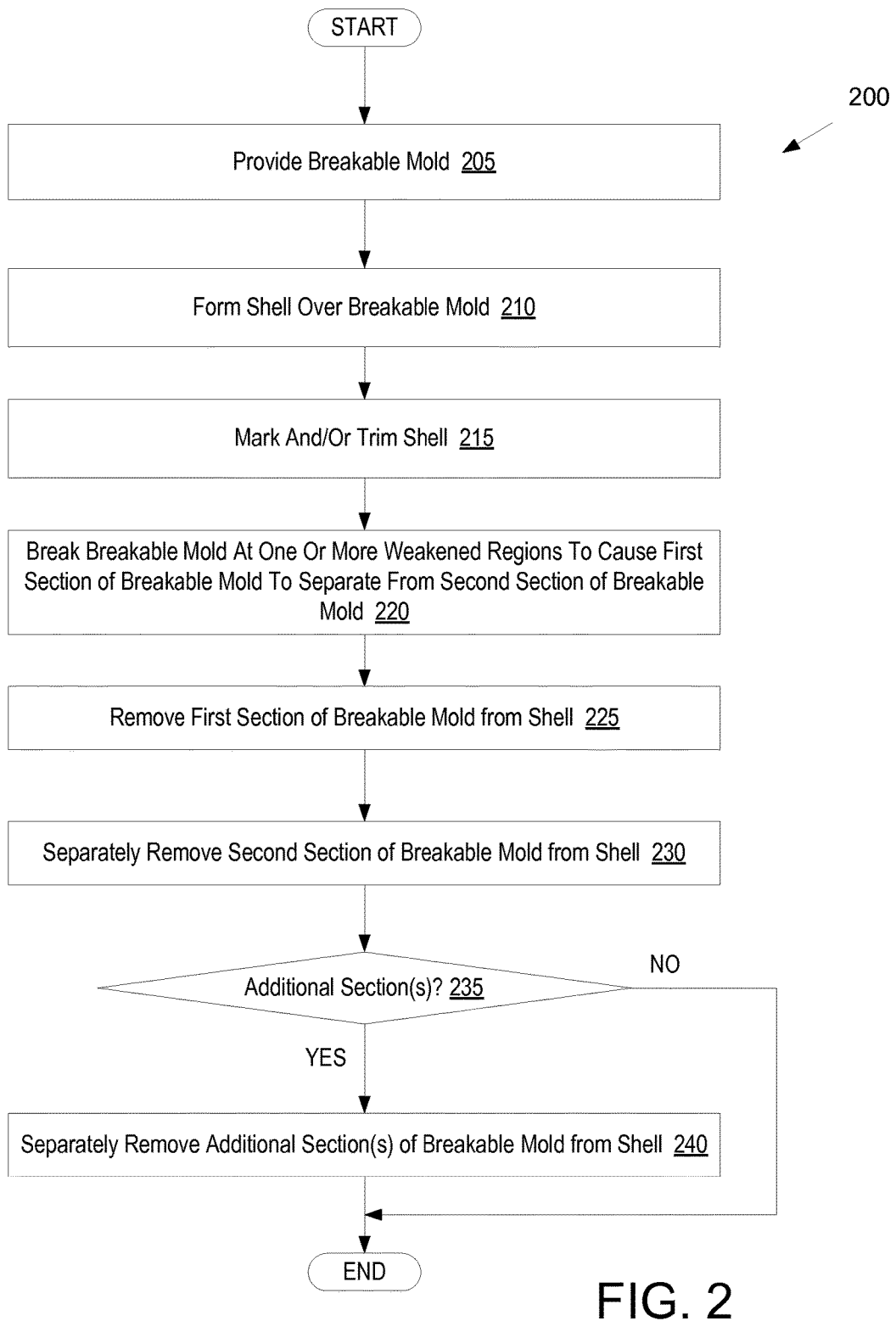
FIG. 2 illustrates a flow diagram for a method of using a breakable mold to fabricate a shell, in accordance with one embodiment.

FIG. 2 illustrates a flow diagram for a method 200 of using a breakable mold to fabricate a shell, in accordance with one embodiment. At block 205 of method 200, a breakable mold is provided. The breakable mold may have been manufactured in accordance with method 100 of FIG. 1. The breakable mold includes at least two sections that are joined by a weakened region. The breakable mold may include any number of sections in one embodiment, and may include weakened regions at each intersection of two or more sections. The placement of weakened regions and numbers of sections may be to accommodate features in the breakable mold having undercuts or negative inclination.

At block 210, a shell is formed over the breakable mold. In one embodiment, a sheet of material is pressure formed or thermoformed over the breakable mold. The sheet may be, for example, a sheet of plastic (e.g., an elastic thermoplastic). To thermoform the shell over the breakable mold, the sheet of material may be heated to a temperature at which the sheet becomes pliable. Pressure may concurrently be applied to the sheet to form the now pliable sheet around the breakable mold. Once the sheet cools, it will have a shape that conforms to the breakable mold. In one embodiment, a release agent (e.g., a non-stick material) is applied to the breakable mold before forming the shell. This may facilitate later removal of the breakable mold from the shell.

At block 215, the shell may be marked and/or trimmed while it is still on the breakable mold. For example, if the breakable mold is of a dental arch and the shell is an orthodontic aligner to align a patient's teeth, then a gingival cut line (or other cut line) may be identified and cut. A laser cutter, plasma cutter, or mechanical cutter (e.g. a 5 axis milling machine) may be used to cut the gingival cut line or other cut line. In one embodiment, the aligner is not cut until after the shell is removed from the breakable mold. Alternatively, the aligner may be cut prior to removal of the breakable mold. Alternatively, some trimming may occur before removal of the breakable mold from the shell and additional trimming may occur after the removal of the breakable mold from the shell. Marking of the shell may include using a laser to add a label such as a serial number or part number to the shell.

At block 220, the breakable mold is broken at the one or more weakened regions to cause at least the first section of the breakable mold to separate from the second section of the breakable mold. Various techniques may be used to break the weakened regions of the breakable mold. In one embodiment, a user may simply break the breakable mold by attempting to remove the breakable mold from the shell. The weakened regions may be weakened such that the weakened regions will break from the application of force before enough force is applied to damage or permanently deform the shell. In another embodiment, ultrasonic waves may be applied to the breakable mold to collapse, crumble or otherwise break the weakened regions. Alternatively, the breakable mold may be vibrated to break the weakened regions. In another example, a fixture with a knife edge or other shaped edge may be applied to the breakable structure (e.g., at a weakened region) to crush, cut or otherwise break one or more of the weakened regions. The fixture may apply a predetermined amount of force in a particular direction or angle to break the weakened regions, for example. In another example, the weakened regions may be crushed by applying pressure to the breakable mold.

If there are multiple weakened regions, then all of the weakened regions may be broken approximately simultaneously (e.g., in response to a single application of force to the breakable mold). Alternatively, different weakened regions may be broken at different times. For example, a first application of force may break a first subset of weakened regions, and a second application of force may break a second subset of weakened regions.

In one embodiment, the weakened regions are broken after the shell has been formed over the breakable mold (e.g., during the process of removing the breakable mold from the shell). In another embodiment, the weakened regions are broken during the process of forming the shell over the breakable mold. For example, the weakened regions may be crushed by the application of pressure used to form the shell over the mold. In other embodiments, some weakened regions may be broken during the formation of the shell, and other weakened regions of the breakable mold may be broken after the shell has been formed.

At block 225, the first section of the breakable mold is removed from the shell. Note that in some instances the operations of block 220 are combined with those of block 225, such that removal of the first section from the shell causes a weakened region to break. At block 230, the second section of the breakable mold is removed from the shell.

At block 235, a determination is made as to whether there are additional sections of the breakable mold still in the shell. If so, then the method proceeds to block 240 and each of the additional sections is separately removed from the shell. Additional processing of the shell may then be performed, such as any further cutting of the shell (e.g., at a previously marked gingival cut line). Other additional processing may include polishing the shell, cleaning the shell, stamping the shell, etc. The shell may then be packaged and shipped.

Figure 3B:
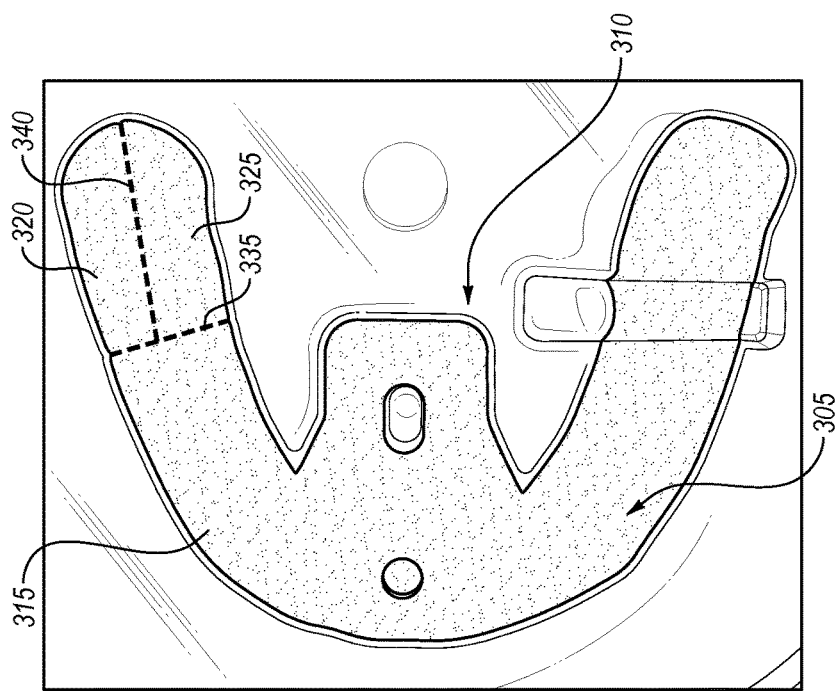
FIG. 3B illustrates a second view of a shell formed over a breakable mold, in accordance with one embodiment.
Figure 3A:
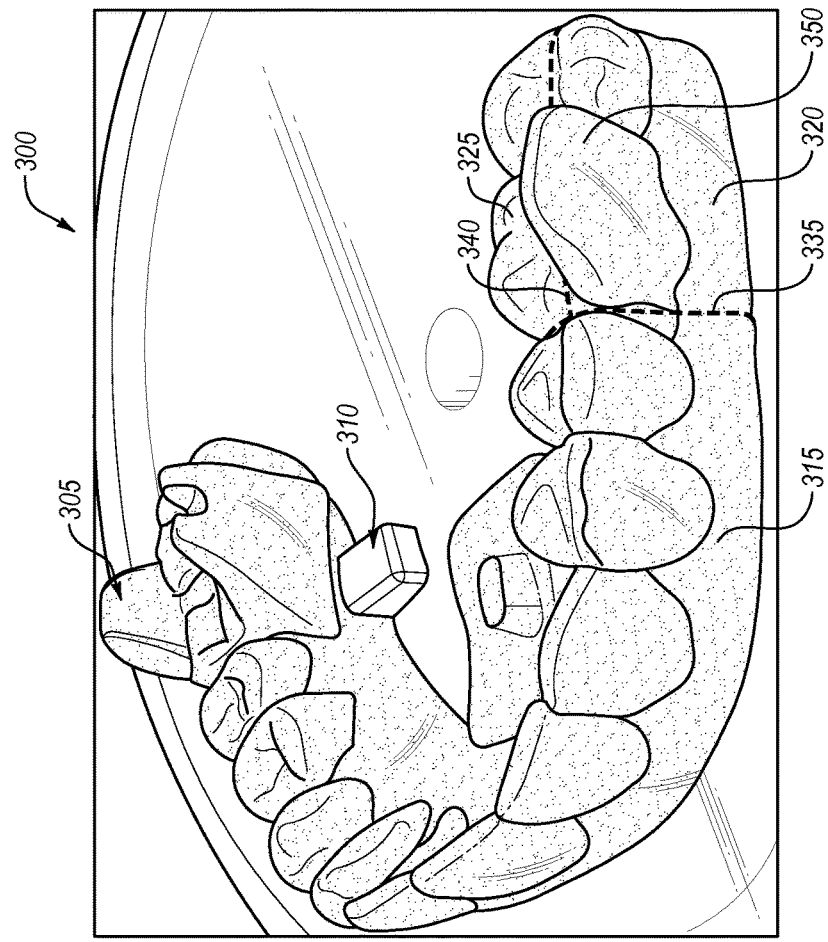
FIG. 3A illustrates a first view of a shell formed over a breakable mold, in accordance with one embodiment.

FIGS. 3A-6B illustrate a shell 310 at various stages of manufacturing, in accordance with one embodiment. The shell 310 is an orthodontic aligner that will be placed over a dental arch of a patient to reposition the patient's teeth and/or jaw. FIG. 3A illustrates a first view 300 of the shell 310 formed over a breakable mold 305. FIG. 3B illustrates a second view 302 of the shell 310 formed over the breakable mold 305. As shown, the breakable mold 305 includes three sections 315, 320, 325. Section 320 is joined to section 325 by weakened region 340. Sections 320 and 325 are joined to section 315 by weakened region 335. As shown, the breakable mold 305 includes a feature 350 with an undercut. In an example mold, this feature could prevent the removal of the mold from the shell. However, the illustrated breakable mold 305 may be removed from the shell 310 without damaging the shell 310.

Figure 4B:
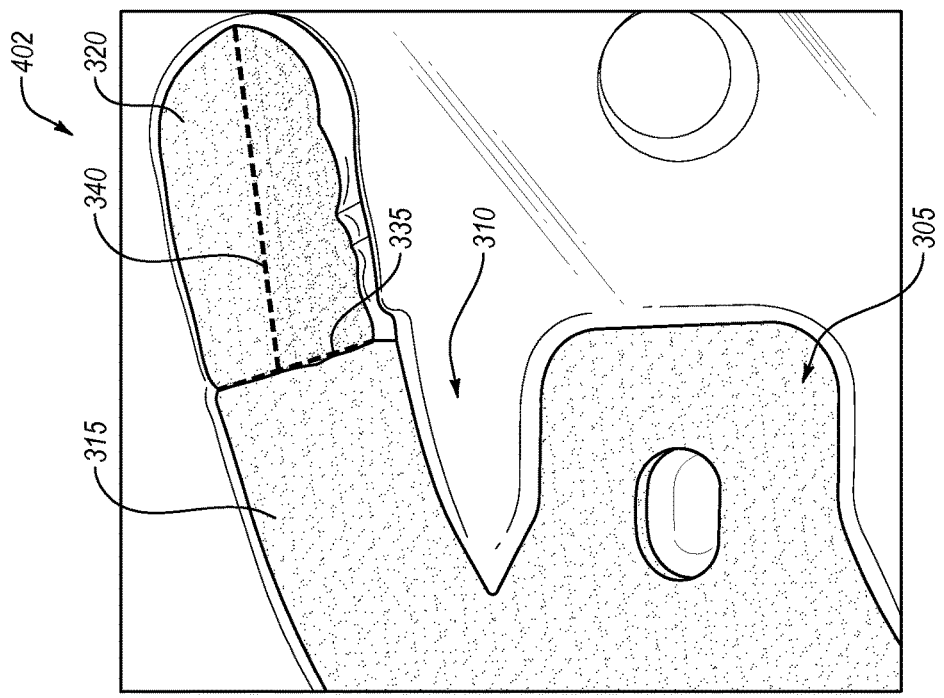
FIG. 4B illustrates the second view of FIG. 3B after the first section of the breakable mold has been removed from the shell, in accordance with one embodiment.
Figure 4A:
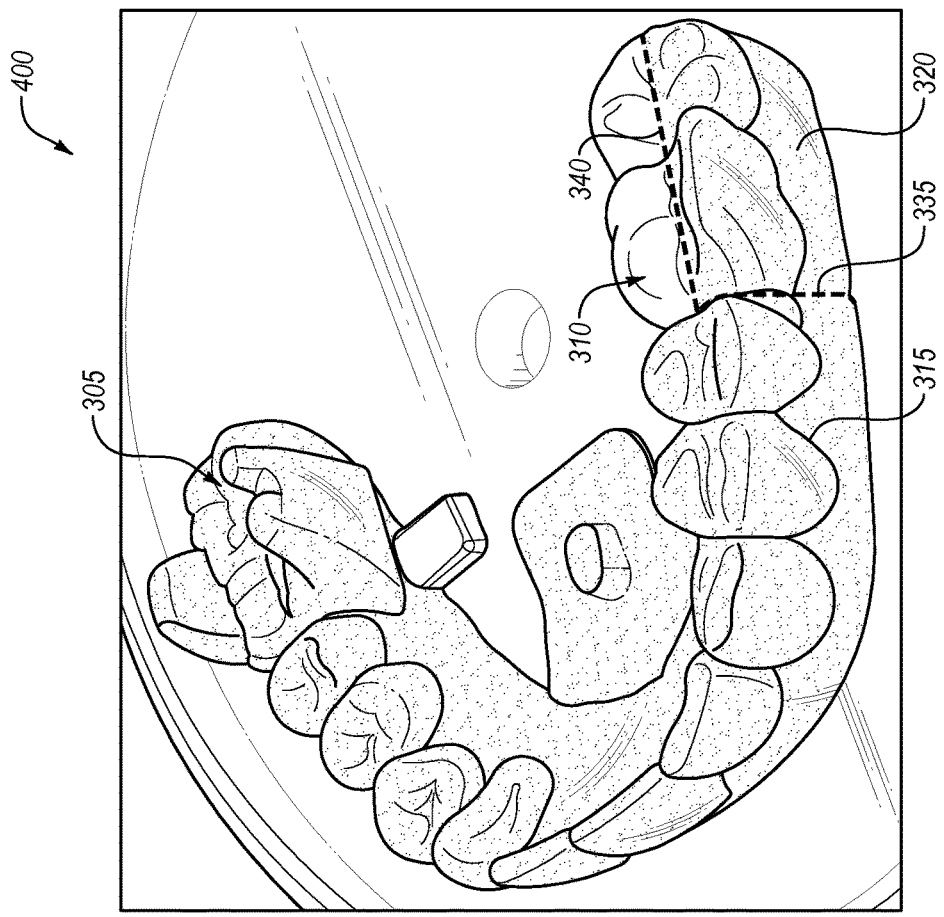
FIG. 4A illustrates the first view of FIG. 3A after a first section of the breakable mold has been removed from the shell, in accordance with one embodiment.

FIG. 4A illustrates a first view 400, similar to first view 300 of FIG. 3A, of the shell 310 after a first section 325 of the breakable mold 305 has been removed from the shell. FIG. 4B illustrates a second view 402, similar to second view 302 of FIG. 3B, after the first section 325 of the breakable mold 305 has been removed from the shell 310. The breakable mold 305 was broken at the weakened regions 340 and 335, and the first section 325 was removed without damaging or deforming the shell 310 (and is thus not shown in views 400 and 402).

Figure 5B:
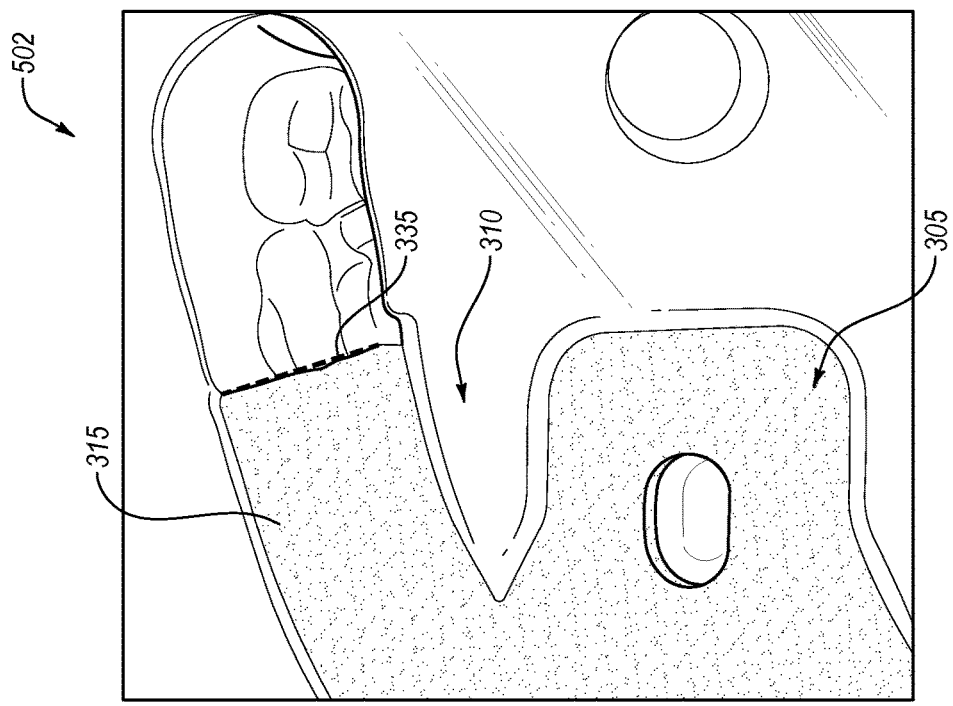
FIG. 5B illustrates the second view of FIG. 4B after the second section of the breakable mold has been removed from the shell, in accordance with one embodiment.
Figure 5A:
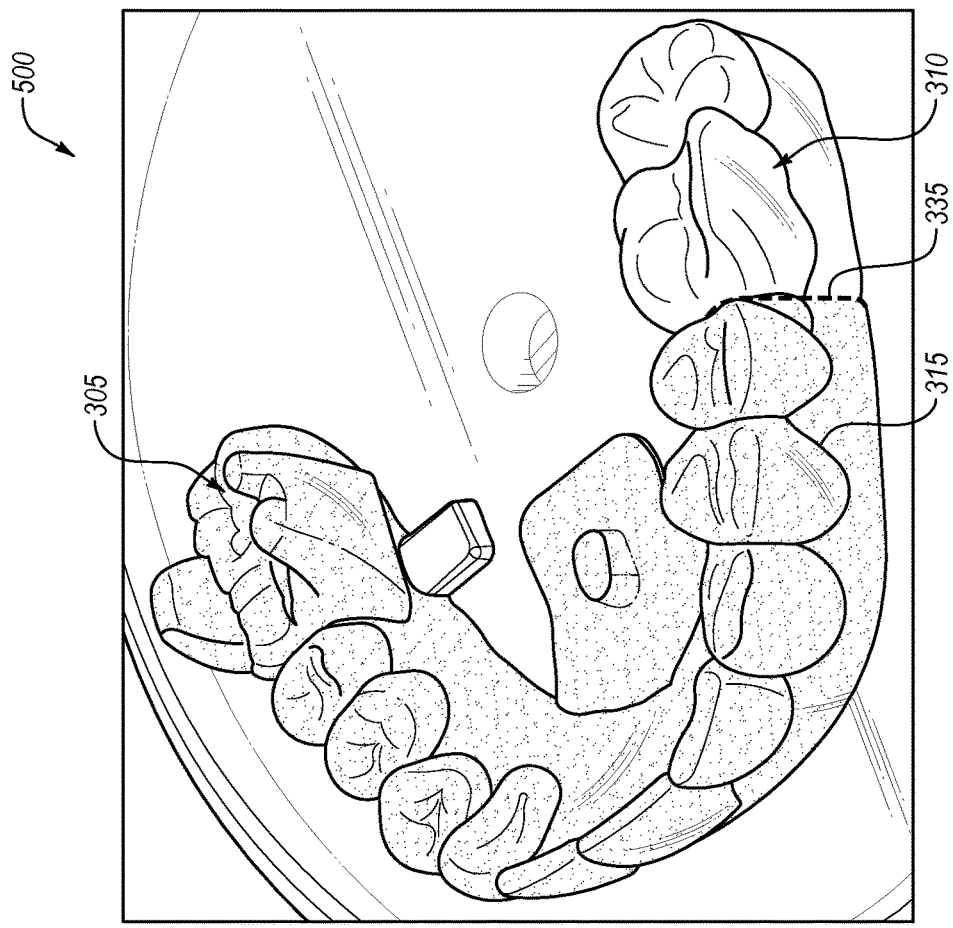
FIG. 5A illustrates the first view of FIG. 4A after a second section of the breakable mold has been removed from the shell, in accordance with one embodiment.

FIG. 5A illustrates a first view 500, similar to first view 400 of FIG. 4A, of the shell 310 after a second section 320 of the breakable mold 305 has been removed from the shell 310. FIG. 4B illustrates a second view 502, similar to second view 402 of FIG. 4B, after the second section 320 of the breakable mold 305 has been removed from the shell 305. As shown, the breakable mold 305 was broken at the weakened region 335, and the second section 320 was removed without damaging or deforming the shell 310 (and is thus not shown in views 400 and 402).

Figure 6A:
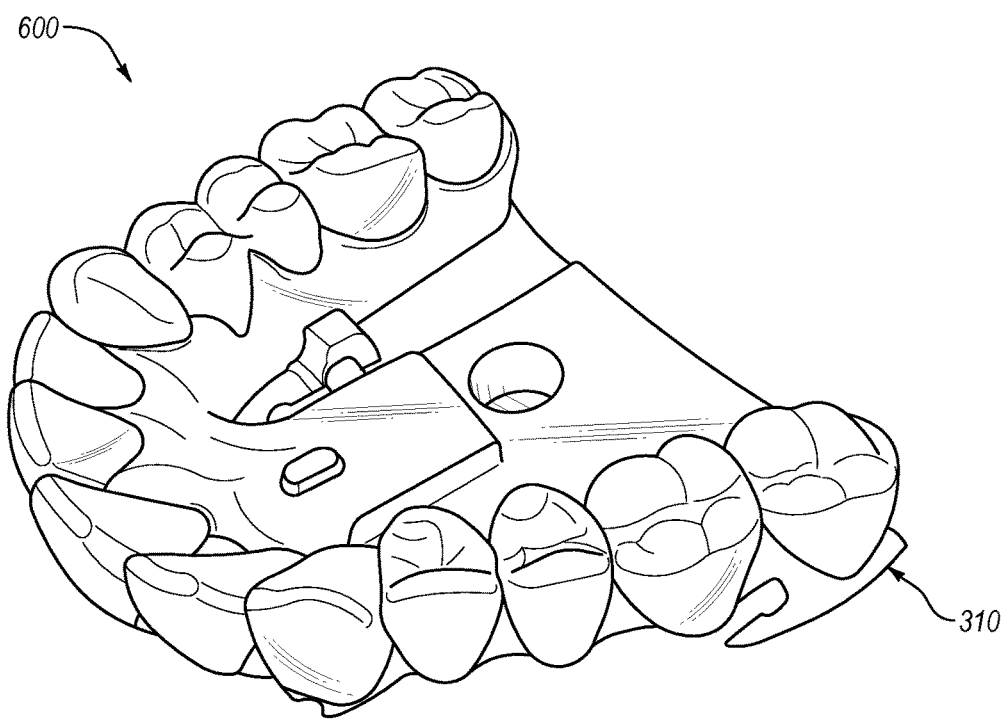
FIG. 6A illustrates the first view of FIG. 5A after a remainder of the breakable mold has been removed from the shell, in accordance with one embodiment.
Figure 6B:
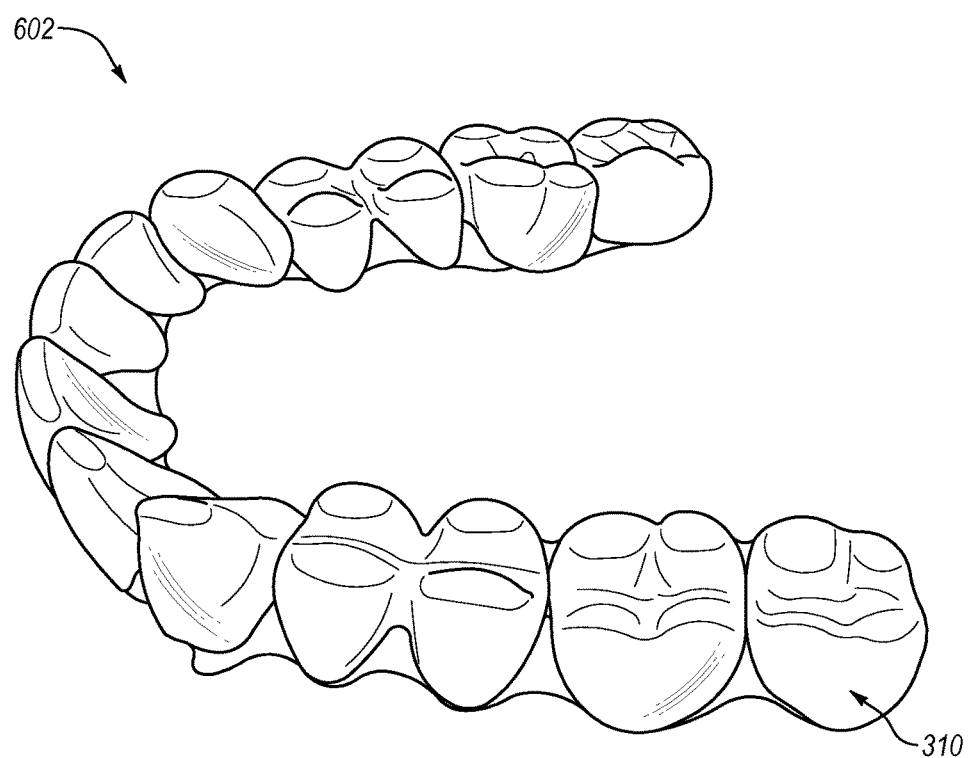
FIG. 6B illustrates the first view of FIG. 6A after the shell has been cut, in accordance with one embodiment.

FIG. 6A illustrates a view 600, similar to view 500 of FIG. 5A, of shell 310 after a remainder of the breakable mold has been removed from the shell 310. FIG. 6B illustrates a view 602, similar to view 600 of FIG. 6A, of the shell 310 after the shell 310 has been cut along the gingival line.

Figure 7A:
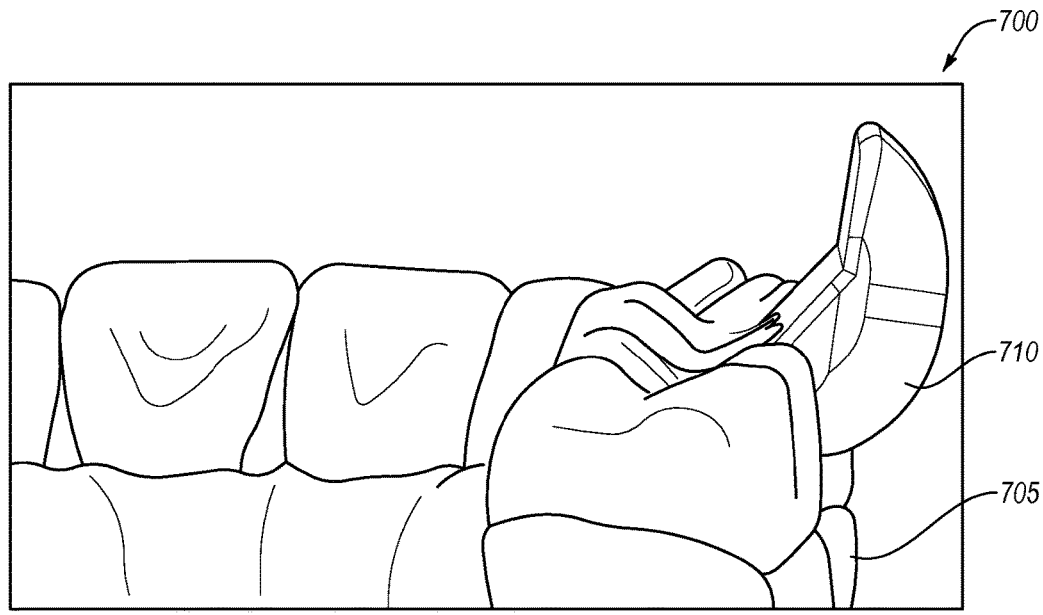
FIG. 7A illustrates an example mold of a dental arch with an attached feature.

FIG. 7A illustrates a mold 700 of a dental arch having a main body 705 with an attached feature 710. The attached feature 710 is large and has an undercut that could render removal of a shell formed over the mold 700 difficult if not impossible.

Figure 7B:
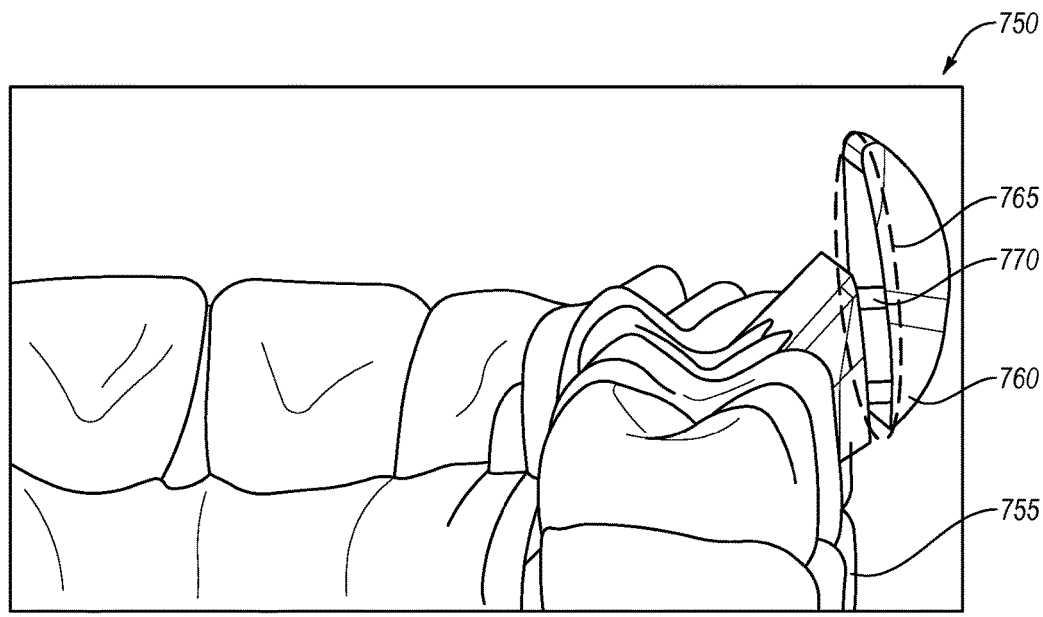
FIG. 7B illustrates an example breakable mold of the dental arch of FIG. 7A.

FIG. 7B illustrates an example breakable mold 750 of the same dental arch of FIG. 7A. The breakable mold 750 includes a first section 755 (e.g., a main body) and an attached second section 760 (e.g. a feature that is similar to the attached feature 710 of FIG. 7A). However, attached second section 760 is joined to the first section 755 via a weakened region 770 that includes a void and two support structures 770, 775 that bridge the void. During removal of the breakable mold 750 from a shell formed thereon, the support structures 770, 775 would break, enabling the first section 755 to be removed from the shell separately from the attached second section 760. This enables the breakable mold 750 to be removed from the shell without damaging the shell.

Figure 8:
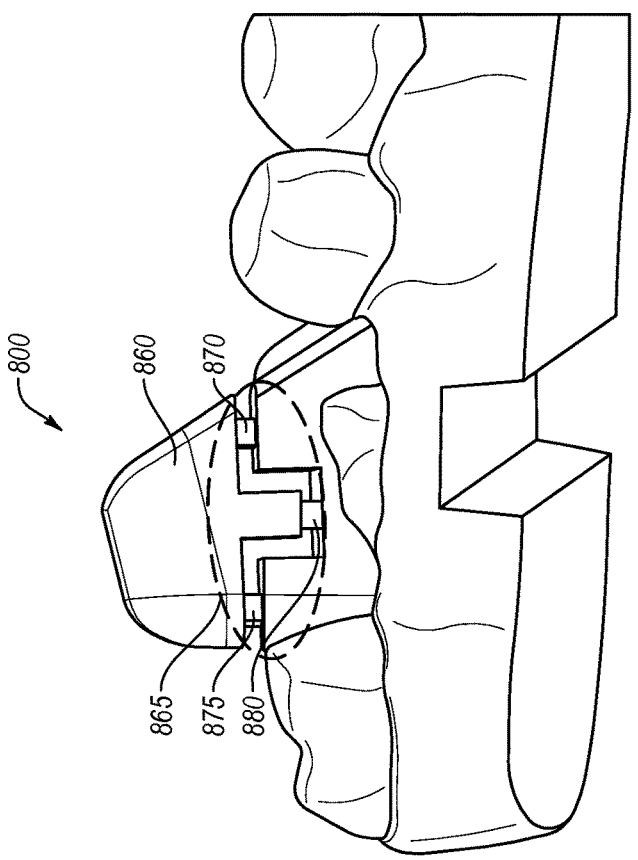
FIG. 8 illustrates an example breakable mold.

FIG. 8 illustrates another example breakable mold 800. The example breakable mold 800 includes a main body 855 that is joined to a feature 860 by a weakened region 880. The weakened region includes a void and three support structures 870-880 that bridge the void. Weakened region 880 may not reflect a size of an actual weakened region. For example, the illustrated weakened region 880 is shown with an enlarged void for the purpose of illustration. However, the width of this void may be reduced in some embodiments.

Figure 9:
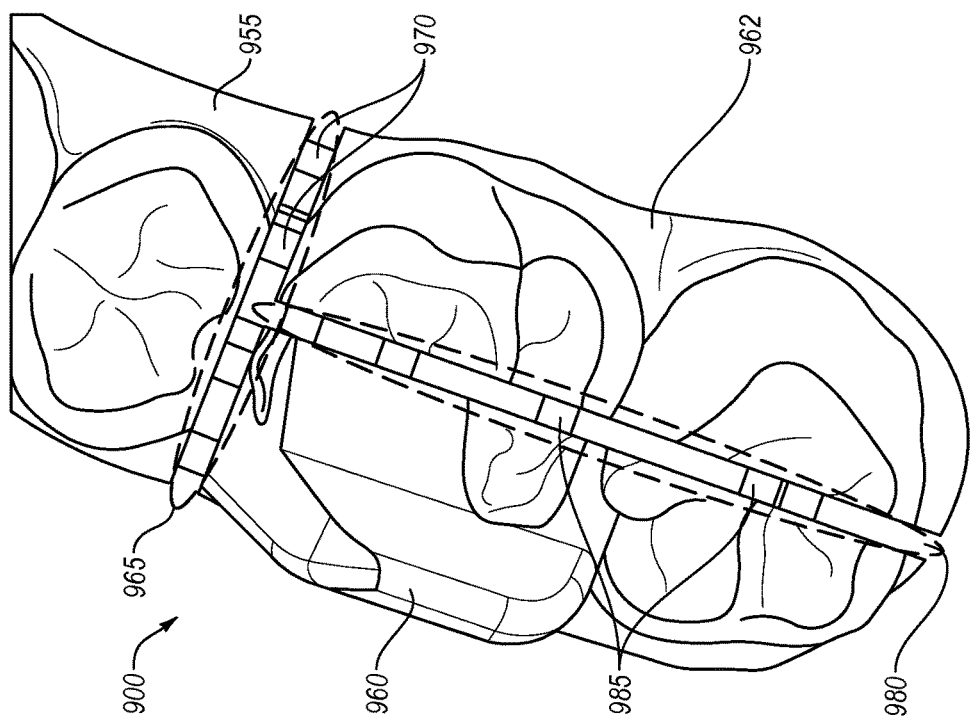
FIG. 9 illustrates an example breakable mold.

FIG. 9 illustrates another example breakable mold 900. The example breakable mold 900 is divided into a first section 955, a second section 960 and a third section 962. The first section 955 is joined to the second and third sections 960, 962 via a first weakened region 965 that includes a void and multiple support structures 970 that span the void. Second section 960 is additionally joined to third section 962 by a second weakened region 980 that includes a void and multiple support structures 985 that span the void. Weakened regions 965, 980 may not reflect sizes of actual weakened regions. For example, the illustrated weakened regions 965, 980 are shown with enlarged voids for the purpose of illustration. However, the width of these voids may be reduced in some embodiments.

As noted earlier, there are multiple dental conditions that are traditionally difficult to treat using orthodontic aligners that reposition teeth and/or a jaw of a patient. Such dental conditions include, but are not limited to, crowded teeth, proclined teeth, retroclined teeth, ectopic teeth, and out of arch teeth. FIGS. 10A-13C illustrate various examples of breakable molds that may be used to form shells (e.g., aligners) for treating such dental conditions.

Figure 10C:
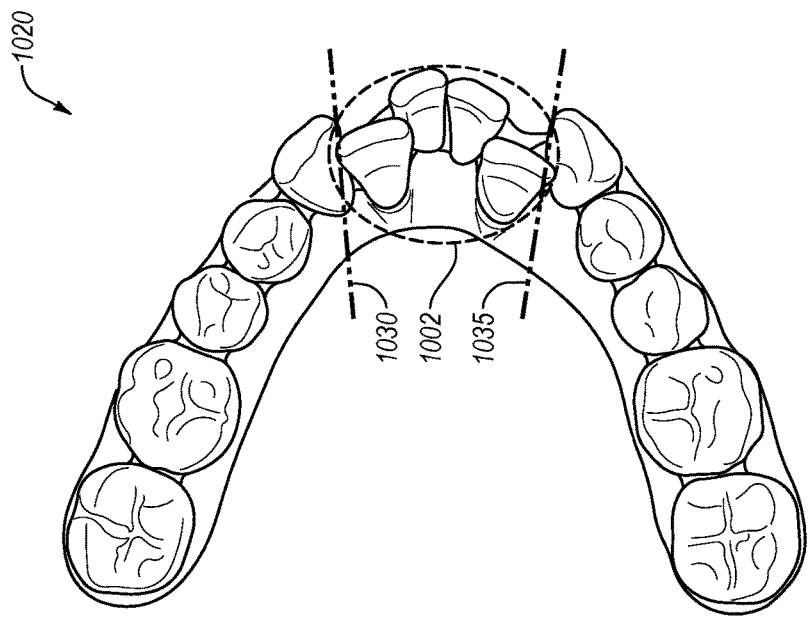
FIG. 10C illustrates a third view of the example breakable mold of FIG. 10A.
Figure 10A:
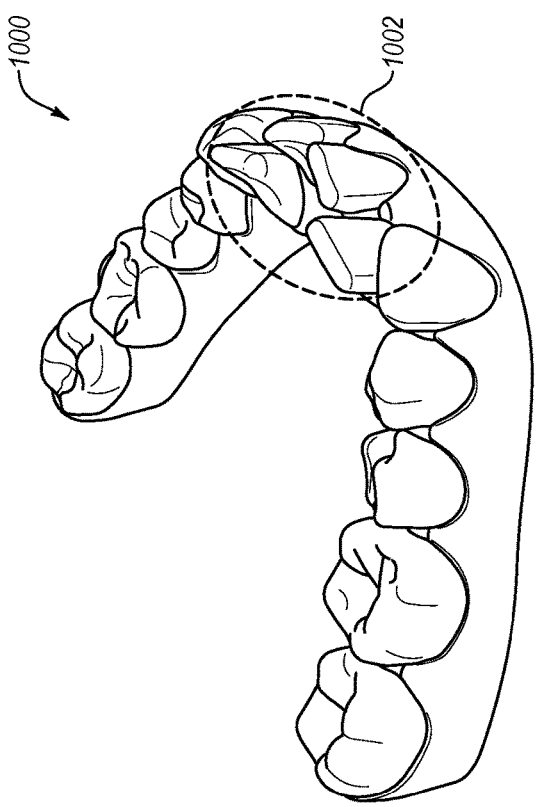
FIG. 10A illustrates a first view of an example breakable mold of a dental arch with crowded teeth.
Figure 10B:
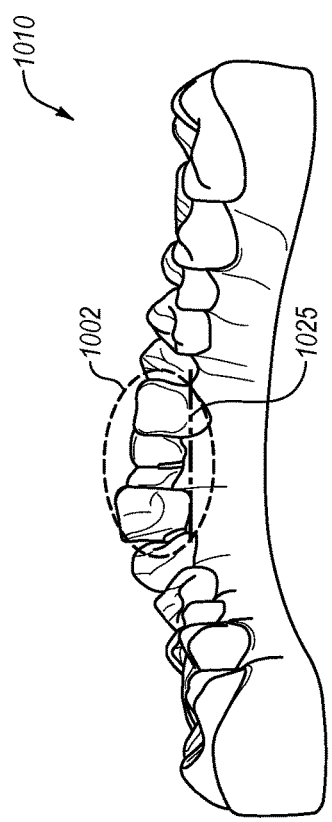
FIG. 10B illustrates a second view of the example breakable mold of FIG. 10A.

FIG. 10A illustrates an example mold 1000 for a dental arch with crowded teeth 1002. FIG. 10B illustrates a first example breakable mold 1010 for the dental arch with crowded teeth 1002. A weakened region is placed at line 1025 to divide the breakable mold 1010 into multiple sections. Accordingly, a section of the breakable mold 1010 that includes the crowded teeth 1002 will be removable from a shell formed on the breakable mold separate from one or more other sections of the breakable mold 1010. FIG. 10C illustrates a second example breakable mold 1020 for the dental arch with the crowded teeth 1002. Weakened regions are placed at lines 1030 and 1035 to divide the breakable mold 1020 into multiple sections. Accordingly, a section of the breakable mold 1020 that includes the crowded teeth 1002 will be removable from a shell formed on the breakable mold separate from one or more other sections of the breakable mold 1020. Alternative breakable molds might include weakened regions at each of lines 1025, 1030 and 1035, or at other locations, for similar effect.

Figure 11B:
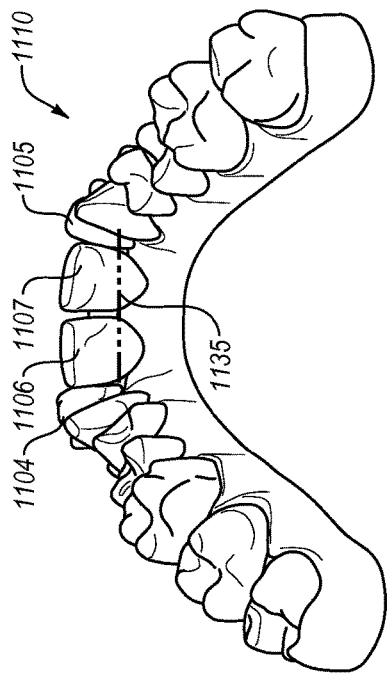
FIG. 11B illustrates a second view of the example breakable mold of FIG. 11A.
Figure 11D:
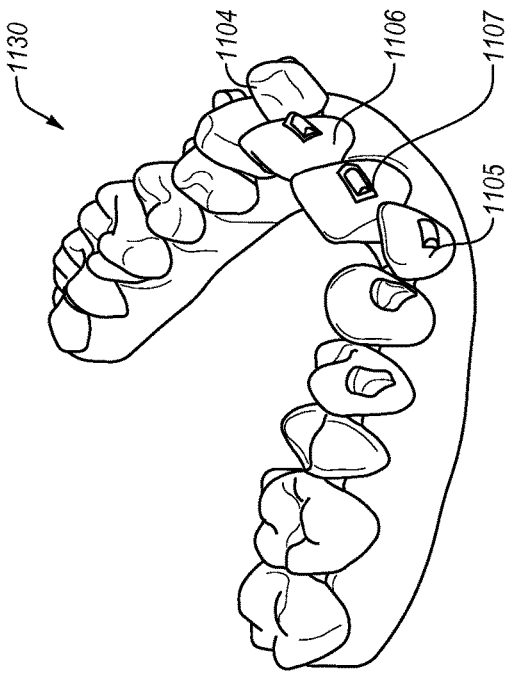
FIG. 11D illustrates a fourth view of the example breakable mold of FIG. 11A.
Figure 11A:
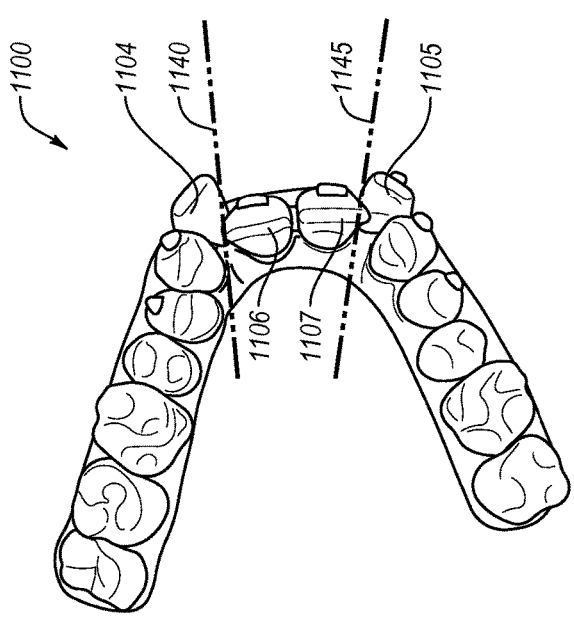
FIG. 11A illustrates a first view of an example breakable mold of a dental arch with a proclined/retroclined tooth.
Figure 11C:
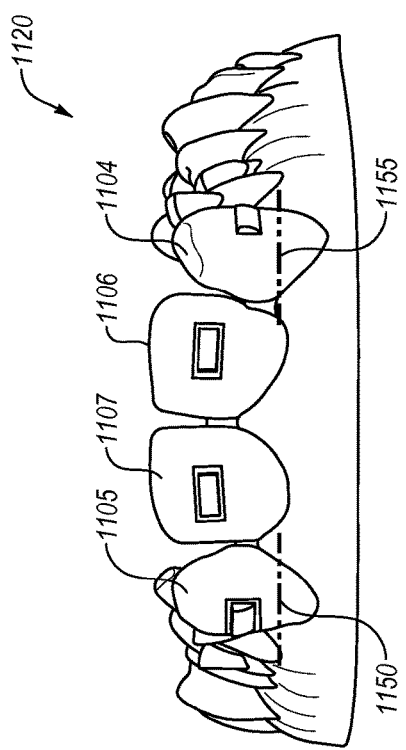
FIG. 11C illustrates a third view of the example breakable mold of FIG. 11A.

FIG. 11A illustrates a first example breakable mold 1100 of a dental arch with a pair of proclined teeth 1104, 1105 and a pair of retroclined teeth 1106, 1107. FIG. 11B illustrates a second example breakable mold 1110 of the dental arch with the pair of proclined teeth 1104, 1105 and the pair of retroclined teeth 1106, 1107. FIG. 11C illustrates a third example breakable mold 1120 of the dental arch with the pair of proclined teeth 1104, 1105 and the pair of retroclined teeth 1106, 1107. FIG. 11D illustrates a standard mold 1130 of the dental arch with the pair of proclined teeth 1104, 1105 and the pair of retroclined teeth 1106, 1107. Each of the example breakable molds 1100, 1110, 1120 uses differently placed weakened regions. For example, breakable mold 1100 includes weakened regions placed at lines 1140, 1145. Breakable mold 1110 includes a weakened region placed at line 1135. Breakable mold 1120 includes weakened regions placed at lines 1150 and 1155. In example breakable molds 1110, 1120, a section of the breakable mold 1110, 1120 that includes the retroclined teeth 1106, 1107 will be removable from a shell formed on the breakable mold separate from one or more other sections of the breakable mold. For example breakable mold 1130, each of the proclined teeth 1150, 1155 are contained in separate sections that may be removed from the shell separately from other sections of the breakable mold. Alternative breakable molds might include weakened regions at two or more of lines 1135, 1140, 1145, 1150 and 1155, or at other locations, for similar effect.

FIG. 12A illustrates an example mold 1200 of a dental arch with an ectopic tooth 1204. FIG. 12B illustrates a first example breakable mold 1210 of the dental arch with the ectopic tooth 1204. FIG. 12C illustrates a second example breakable mold 1220 of the dental arch with the ectopic tooth 1204. For breakable mold 1210, a weakened region is placed at line 1230 to divide the breakable mold 1210 into multiple sections. For breakable mold 1220, a weakened region is placed at line 1225 to divide the breakable mold 1210 into multiple sections. Accordingly, a section of either breakable mold 1210, 1220 that includes the ectopic tooth 1204 will be removable from a shell formed on the breakable mold separate from one or more other sections of the breakable mold. Alternative breakable molds might include weakened regions at each of lines 1225 and 1230, or at other locations, for similar effect.

FIG. 13A illustrates a first example breakable mold 1300 of a dental arch with an out of arch tooth 1304. Such a dental condition causes a shell that is created to be formed both around all of the teeth and between the out of arch tooth and other teeth. Accordingly, conventional molds may not be used to form shells for dental arches that includes out of arch teeth in some instances. FIG. 13B illustrates a second example breakable mold 1310 of the dental arch with the out of arch tooth 1304. FIG. 13C illustrates a third example breakable mold 1320 of the dental arch with the out of arch tooth 1304. For breakable mold 1300, a weakened region is placed at line 1325 to divide the breakable mold 1300 into multiple sections. For breakable mold 1310, a weakened region is placed at line 1335 to divide the breakable mold 1310 into multiple sections. For breakable mold 1320, a weakened region is placed at line 1330 to divide the breakable mold 1320 into multiple sections. Accordingly, a section of each of the breakable molds 1300, 1310, 1320 that includes the out of arch tooth 1304 will be removable from a shell formed on the breakable mold separate from one or more other sections of the breakable mold. Alternative breakable molds might include weakened regions at two or more of lines 1325, 1330 and 1335, or at other locations, for similar effect.

Figure 14:
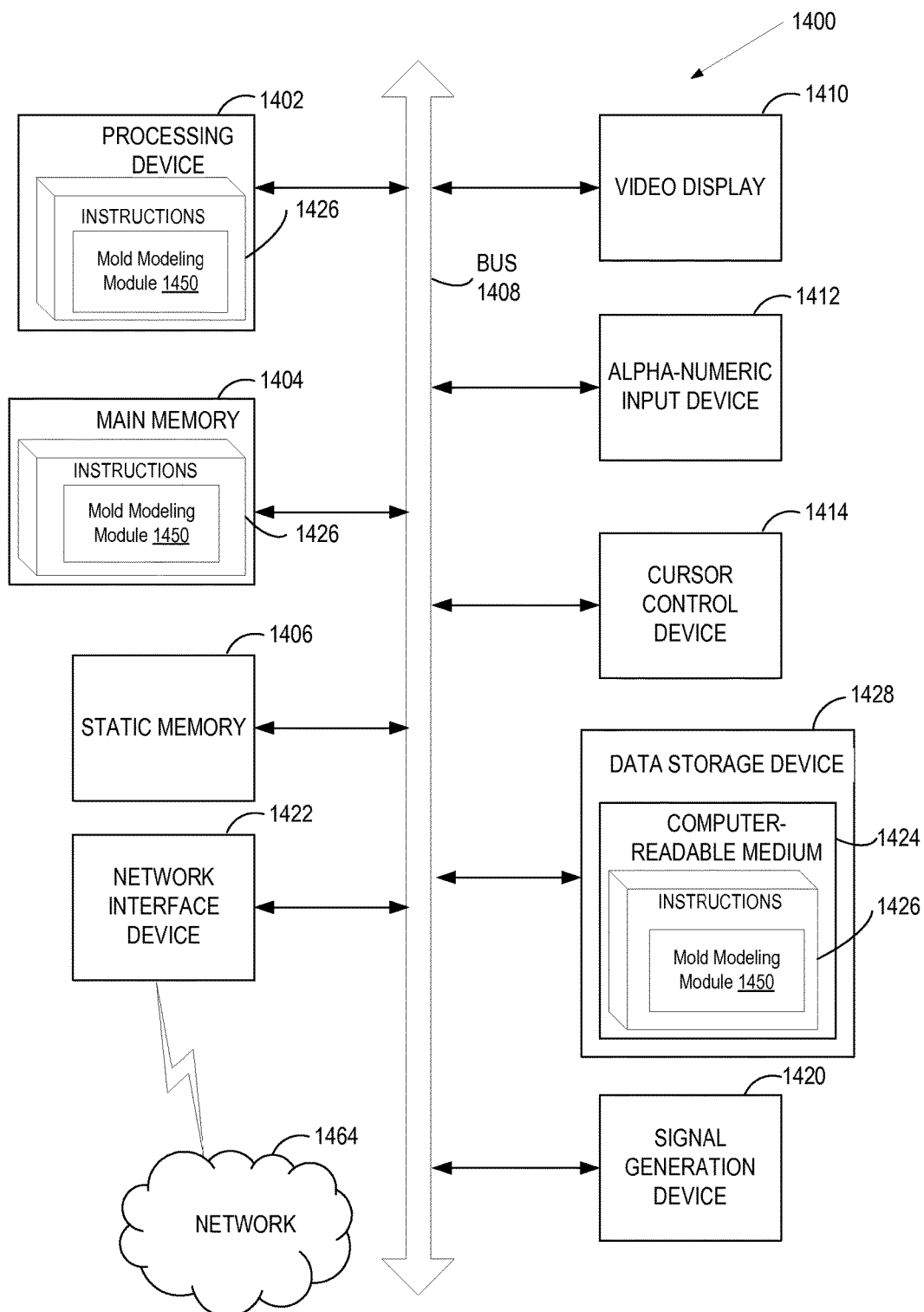
FIG. 14 illustrates a block diagram of an example computing device, in accordance with embodiments of the present invention.

FIG. 14 illustrates a diagrammatic representation of a machine in the example form of a computing device 1400 within which a set of instructions, for causing the machine to perform any one or more of the methodologies discussed with reference to FIG. 1. In alternative embodiments, the machine may be connected (e.g., networked) to other machines in a Local Area Network (LAN), an intranet, an extranet, or the Internet. For example, the machine may be networked to a rapid prototyping apparatus such as a 3D printer or SLA apparatus. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 1400 includes a processing device 1402, a main memory 1404 (e.g., read-only memory (ROM), flash memory, dynamic random access memory (DRAM) such as synchronous DRAM (SDRAM), etc.), a static memory 1406 (e.g., flash memory, static random access memory (SRAM), etc.), and a secondary memory (e.g., a data storage device 1428), which communicate with each other via a bus 1408.

Processing device 1402 represents one or more general-purpose processors such as a microprocessor, central processing unit, or the like. More particularly, the processing device 1402 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1402 may also be one or more special-purpose processing devices such as an application specific integrated circuit (ASIC), a field programmable gate array (FPGA), a digital signal processor (DSP), network processor, or the like. Processing device 1402 is configured to execute the processing logic (instructions 1426) for performing operations and steps discussed herein.

The computing device 1400 may further include a network interface device 1422 for communicating with a network 1464. The computing device 1400 also may include a video display unit 1410 (e.g., a liquid crystal display (LCD) or a cathode ray tube (CRT)), an alphanumeric input device 1412 (e.g., a keyboard), a cursor control device 1414 (e.g., a mouse), and a signal generation device 1420 (e.g., a speaker).

The data storage device 1428 may include a machine-readable storage medium (or more specifically a non-transitory computer-readable storage medium) 1424 on which is stored one or more sets of instructions 1426 embodying any one or more of the methodologies or functions described herein. A non-transitory storage medium refers to a storage medium other than a carrier wave. The instructions 1426 may also reside, completely or at least partially, within the main memory 1404 and/or within the processing device 1402 during execution thereof by the computer device 1400, the main memory 1404 and the processing device 1402 also constituting computer-readable storage media.

The computer-readable storage medium 1424 may also be used to store one or more virtual 3D models and/or a mold modeling module 1450, which may perform one or more of the operations of method 100 described with reference to FIG. 1. The computer readable storage medium 1424 may also store a software library containing methods that call a mold modeling module 1450. While the computer-readable storage medium 1424 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A method comprising:
   forming a shell over a breakable mold of a dental arch for a patient, wherein a first section of the breakable mold is joined to a second section of the breakable mold by one or more weakened regions, wherein the first section is a first mold of at least a portion of one or more first teeth of the dental arch and the second section is a second mold of at least a portion of one or more second teeth of the dental arch;
   breaking the breakable mold at the one or more weakened regions to enable the first section of the breakable mold to at least partially separate from the second section of the breakable mold;

removing the first section of the breakable mold from the shell; and separately removing the second section of the breakable mold from the shell.

2. The method of claim 1, wherein the breakable mold comprises a 3D printed mold.

3. The method of claim 1, wherein the shell comprises at least one of an orthodontic aligner, an orthodontic retainer, or an orthodontic splint to be used for at least one of aligning, retaining, or positioning one or more teeth of the patient.

4. The method of claim 1, wherein forming the shell comprises at least one of thermoforming or pressure forming the shell over the breakable mold.

5. The method of claim 1, further comprising:
identifying at least one of an undercut or a complex region that will be included in the breakable mold;
determining where in the breakable mold to place the one or more weakened regions relative to at least one of the undercut or the complex region; and
forming the breakable mold.

6. The method of claim 5, wherein the one or more weakened regions are formed during the forming of the breakable mold.

7. The method of claim 5, further comprising:
processing the breakable mold after formation of the breakable mold to introduce the one or more weakened regions to the breakable mold.

8. The method of claim 1, wherein the breakable mold is broken during the forming of the shell over the breakable mold.

9. The method of claim 1, wherein the breakable mold is broken during removal of the breakable mold from the shell based on application of a threshold force, wherein the threshold force is a lesser force than a force that would damage or permanently deform the shell.

10. The method of claim 1, wherein the breakable mold comprises a feature having an undercut, and wherein the at least a portion of one or more first teeth comprises a first side of the feature and the at least a portion of one or more second teeth comprises a second side of the feature.

* * * * *